US010264795B2

(12) United States Patent
Kwak et al.

(10) Patent No.: US 10,264,795 B2
(45) Date of Patent: Apr. 23, 2019

(54) STREPTOMYCES BADIUS SP6C4 STRAIN HAVING ANTIMICIROBIAL ACTIVITY AGAINST INSECT PATHOGEN OR STRAWBERRY FUNGAL DISEASE PATHOGEN ISOLATED FROM STRAWBERRY POLLEN AND USES THEREOF

(71) Applicant: INDUSTRY-ACADEMIC COOPERATION FOUNDATION GYEONGSANG NATIONAL UNIVERSITY, Gyeongsangnam-do (KR)

(72) Inventors: Youn-Sig Kwak, Gyeongsangnam-do (KR); Da-Ran Kim, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 0 days.

(21) Appl. No.: 15/575,182

(22) PCT Filed: Apr. 20, 2016

(86) PCT No.: PCT/KR2016/004077
§ 371 (c)(1),
(2) Date: Nov. 17, 2017

(87) PCT Pub. No.: WO2016/208861
PCT Pub. Date: Dec. 29, 2016

(65) Prior Publication Data
US 2018/0146680 A1 May 31, 2018

(30) Foreign Application Priority Data
Jun. 23, 2015 (KR) ........................ 10-2015-0088836

(51) Int. Cl.
| | | |
|---|---|---|
| *A01N 63/00* | (2006.01) |
| *A01N 65/00* | (2009.01) |
| *A01N 25/34* | (2006.01) |
| *A01N 25/00* | (2006.01) |
| *C12N 1/20* | (2006.01) |
| *A23K 50/90* | (2016.01) |
| *A23K 20/10* | (2016.01) |
| *A23B 7/155* | (2006.01) |
| *A23L 3/3571* | (2006.01) |
| *A23K 10/18* | (2016.01) |
| *A61K 39/00* | (2006.01) |
| *C12N 15/82* | (2006.01) |
| *C12R 1/465* | (2006.01) |

(52) U.S. Cl.
CPC .............. *A01N 63/00* (2013.01); *A23B 7/155* (2013.01); *A23K 10/18* (2016.05); *A23K 20/10* (2016.05); *A23K 50/90* (2016.05); *A23L 3/3571* (2013.01); *C12N 1/20* (2013.01); *A01N 25/34* (2013.01); *A01N 65/00* (2013.01); *A23V 2002/00* (2013.01); *A61K 39/0011* (2013.01); *C12N 15/8286* (2013.01); *C12R 1/465* (2013.01)

(58) Field of Classification Search
CPC ........ A01N 63/00; A01N 25/34; A01N 65/00; A61K 39/0011; C12N 15/8286
See application file for complete search history.

(56) References Cited

FOREIGN PATENT DOCUMENTS

| | | |
|---|---|---|
| JP | 2011-188761 A | 9/2011 |
| KR | 10-2011-0012607 A | 2/2011 |
| KR | 10-2011-0092177 A | 8/2011 |
| KR | 10-2012-0053321 A | 5/2012 |
| KR | 10-1311192 B1 | 9/2013 |
| KR | 10-2015-0044831 A | 4/2015 |

OTHER PUBLICATIONS

International Search Report for PCT/KR2016/004077.
Hala M. Rifaat et al., "Taxonomical Studies on Certain Streptomycetes Exhibiting Antimicrobial Activity Isolated From Egyptian Soils", Journal of Culture Collections, vol. 5,, pp. 25-34, 2006-2007.

*Primary Examiner* — Gary B Nickol
*Assistant Examiner* — Lakia J Jackson-Tongue
(74) *Attorney, Agent, or Firm* — The PL Law Group, PLLC

(57) ABSTRACT

*Streptomyces badius* SP6C4 strain has an antimicrobial activity against an insect pathogen or a strawberry fungal disease pathogen isolated from strawberry pollen. The growth of an insect pathogen and a strawberry fungal disease pathogen is suppressed by *Streptomyces badius* SP6C4 strain isolated from strawberry pollen. *Streptomyces badius* SP6C4 strain can be used as an environmentally friendly biological agrochemical which is free of any environmental contamination yielded as a side effect of an agrochemical or any human toxicity caused by residual agrochemicals, and, by having an excellent effect of controlling American foul brood, chalk brood, and strawberry flower mold disease, it can be very advantageously used in terms of an industrial use.

5 Claims, 3 Drawing Sheets
Specification includes a Sequence Listing.

FIG. 3

```
GCTCAGGACGAACGCTGGCGGCGTGCTTAACACATGCAAGTCGAACGATGAAGCCCTTCGGGGTG
GATTAGTGGCGAACGGGTGAGTAACACGTGGGCAATCTGCCCTTCACTCTGGGACAAGCCCTGGA
AACGGGGTCTAATACCGGATAACACTCTGTCCCGCATGGGACGGGGTTGAAAGCTCCGGCGGTGA
AGGATGAGCCCGCGGCCTATCAGCTTGTTGGTGGGGTAATGGCCTACCAAGGCGACGACGGGTAG
CCGGCCTGAGAGGGCGACCGGCCACACTGGGACTGAGACACGGCCCAGACTCCTACGGGAGGCAG
CAGTGGGGAATATTGCACAATGGGCGAAAGCCTGATGCGCGACGCCGCGTGAGGGATGACGGCCT
TCGGGTTGTAAACCTCTTTCAGCAGGGAAGAAGCGAAAGTGACGGTACCTGCAGAAGAAGCGCCG
GCTAACTACGTGCCAGCAGCCGCGGTAATACGTAGGGCGCAAGCGTTGTCCGGAATTATTGGGCG
TAAAGAGCTCGTAGGCGGCTTGTCACGTCGGATGTGAAAGCCCGGGGCTTAACCCCGGGTCTGCA
TTCGATACGGGCTAGCTAGAGTGTGGTAGGGGAGATCGGAATTCCTGGTGTAGCGGTGAAATGCGC
AGATATCAGGAGGAACACCGGTGGCGAAGGCGGATCTCTGGGCCATTACTGACGCTGAGGAGCGA
AAGCGTGGGAGCGAACAGGATTAGATACCCTGGTAGTCCACGCCGTAAACGTTGGGAACTAGGT
GTTGGCGACATTCCACGTCGTCGGTGCCGCAGCTAACGCATTAAGTTCCCCGCCTGGGGAGTACGG
CCGCAAGGCTAAAACTCAAAGGAATTGACGGGGGCCCGCACAAGCAGCGGAGCATGTGGCTTAAT
TCGACGCAACGCGAAGAACCTTACCAAGGCTTGACATATACCGGAAAGCATCAGAGATGGTGCCC
CCCTTGTGGTCGGTATACAGGTGGTGCATGGCTGTCGTCAGCTCGTGTCGTGAGATGTTGGGTTAA
GTCCCGCAACGAGCGCAACCCTTGTTCTGTGTTGCCAGCATGCCCTTCGGGGTGATGGGGACTCAC
AGGAGACTGCCGGGGTCAACTCGGAGGAAGGTGGGGACGACGTCAGTCATCATGCCCCTTATGTC
TTGGGCTGCACACGTGCTACAATGGCCGGTACA (SEQ ID NO: 1)
```

FIG. 4A

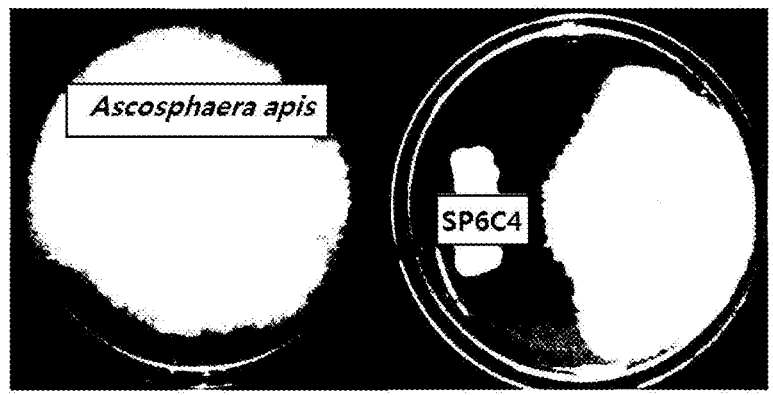

FIG. 4B

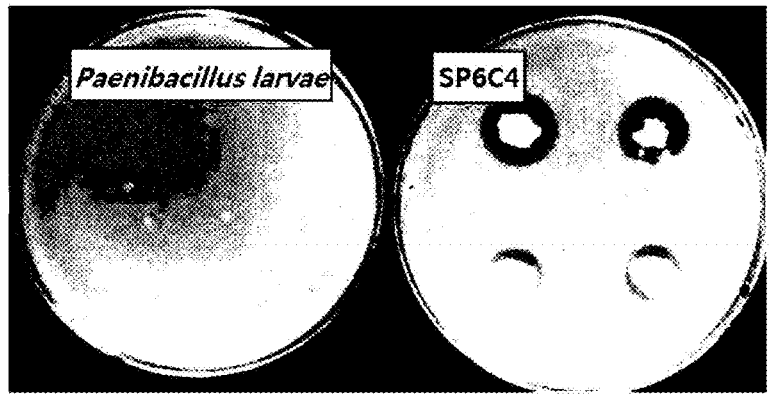

STREPTOMYCES BADIUS SP6C4 STRAIN HAVING ANTIMICROBIAL ACTIVITY AGAINST INSECT PATHOGEN OR STRAWBERRY FUNGAL DISEASE PATHOGEN ISOLATED FROM STRAWBERRY POLLEN AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/004077, filed Apr. 20, 2016, which claims priority to the benefit of Korean Patent Application No. 10-2015-0088836 filed in the Korean Intellectual Property Office on Jun. 23, 2015, the entire contents of which are incorporated herein by reference.

TECHNICAL FIELD

The present invention relates to *Streptomyces badius* SP6C4 strain having an antimicrobial activity against an insect pathogen or a strawberry fungal disease pathogen isolated from strawberry pollen, and uses thereof. Specifically, the present invention relates to *Streptomyces badius* SP6C4 strain having an antimicrobial activity against an insect pathogen or a strawberry fungal disease pathogen, a composition for controlling an insect disease or a strawberry fungal disease containing the strain or a culture thereof as an active ingredient, a method for producing a composition for controlling an insect disease or a strawberry fungal disease comprising culturing the strain, and a method for controlling an insect disease or a strawberry fungal disease comprising treating an area, a plant, or soil infected with insect pathogen with an effective amount of the strain or a culture thereof.

BACKGROUND ART

Among the honeybee diseases, American foul brood (AFB) of honeybees is the most infective and devastating disease. In South Korea, AFB continuously outbreaks all over the country since 1950. Infected larvae produce at least five million hosts to become a secondary inoculum, and, by having strong heat resistance and chemical resistance, larvae spores can be continuously produced every year in the same area. The microbe for causing AFB is *Paenibacillus larvae*, which is gram positive *bacillus* (2.5~5.0 μm×0.7~0.8 μm). *Paenibacillus larvae* has motility by having flagella, and is highly resistant to heat and antibiotics as it can produce endospores. It can also maintain the pathogenicity for several decades even in dry state. Spores germinate in midgut via a mouth of larva to proliferate, and proliferated microbes spread around the larva through the blood circulation to cause death of a larva. honeybees are seriously infected by AFB, it is possible that the entire apiary is quickly and completely dominated by the disease. There have been many studies carried out on prevention and treatment of AFB of honey bees. However, a measure for thorough prevention and control of the disease has not been established yet. Because plate exchange is often made among bee houses in the same apiary, if the disease is not diagnosed at an early stage, the plate exchange is repeated till to yield instant infection of the entire honey bee group. Thus, even in advanced countries, the honey bee group with an outbreak of the disease is often burnt down.

Chalk brood of honey bee is a disease which infiltrates and transforms a larva of a honey bee in bee house into a mummy state, and by subsequently transforming it into a hard chalk state, eventually causes death of the honey bee. Between late spring and early summer, honey bees infected with chalk brood are open spotted in the entrance, floor, or honeycomb of a bee house, and also near the bee house. Since it has been reported first by Massen of Germany in 1913, an outbreak of chalk brood of honey bee is reported in New Zealand in 1957, and in California, USA in 1968 in which the disease is ultimately widely spread in all of the states. In Canada, the outbreak of chalk brood is believed to occur in 1971. In Japan, an outbreak of chalk brood has occurred in Akida-ken in 1974 and it also occurred in honey bees which have been imported from Canada. An outbreak of chalk brood was also found in Kifu-ken in 1979. Thus, chalk brood is found to be one of the most devastating honey bee diseases that are spread all over the world. The pathogen for causing chalk brood is named *Ascosphaera apis*, and it can only infect a larva of a honey bee, showing high sensitivity to a larva of a male honey bee, in particular. It is believed that, as sporangium of a pathogen causing chalk brood has strong resistance to an environment, it can maintain the pathogenicity for 15 years or so. Infection with chalk brood can be caused via various routes such as having contaminated pollen in an infected bee house, requeening of a queen bee in an infected bee house, migration of a queen bee or a worker bee, and propagation of the disease from an infected bee house to a healthy bee house. In Korea, a serious and wide outbreak of the disease starts to occur since mid-80s, and it is now the most devastating honey bee disease to cause a great damage on honey production. As a method for controlling chalk brood that is known up until now, burning down an infected bee house is believed to be the most reliable method. However, as this method is too disadvantageous in terms of economic loss, currently the studies are actively made on a controlling method using chemicals, a method of removing contamination sources by searching the propagation route of a pathogen, or the like as a method for replacing the burning method.

Meanwhile, the crop damage caused by pathogenic plant diseases is estimated to be about 200 trillion Won over the world, showing an extremely high economic loss. In particular, strawberry flower mold disease cannot be easily controlled as it rapidly propagates with an aid of wind or honey bee after an outbreak, and, by preventing pollination of a flower, it yields malformed strawberries. In particular, the pathogen for causing a strawberry flower mold disease (*Cladosporium cladosporioides*) has optimum temperature of 20 to 25° C., and it has a tendency of having a high occurrence in a greenhouse with high humidity or high condensation, or in an environment with insufficient sunlight. The pathogen for causing a strawberry flower mold disease also can grow in dead plants, soil, organic matters, or the like. At present moment, the method for controlling the strawberry flower mold disease is only based on lowering the humidity in a greenhouse and, before the flowering period, carrying out a preventive treatment with an environmentally friendly material that has been registered in terms of a strawberry flower mold disease or anthrax, or with a chemical having little influence on pollen germination or the like. As such, an agent for direct control of the pathogen for causing the strawberry flower mold disease is necessary, and the attention is focused on development of an environmentally friendly agrochemical which is free of a problem like residual toxicity and environmental contamination.

Meanwhile, in Korean Patent Application Publication No. 2011-0092177, description is made with regard to *Lactobacillus plantarum* YML 001 having an antimicrobial activity against pathogen of American Foulbrood, a microbial agent comprising the same, and a control method of using the same, and, in Korean Patent Registration No. 1311192, description is made with regard to a method for producing a composition for preventing and treating honey bee infection and a nutritional composition for honey bee based on the same method. However, *Streptomyces badius* SP6C4 strain having an antimicrobial activity against an insect pathogen or a strawberry fungal disease pathogen isolated from strawberry pollen and uses thereof have not been described yet.

SUMMARY

The present invention is devised in view of the demand described above, and *Streptomyces badius* P6C4 strain of the present invention isolated from strawberry pollen exhibits an effect of suppressing the growth of a pathogen causing AFB (i.e., *Paenibacillus larvae*) and the growth of a pathogen causing chalk brood (i.e., *Ascosphaera apis*), and it also exhibits an antimicrobial activity against a pathogen causing a strawberry flower mold disease (i.e., *Cladosporium cladosporioides*). Based on this, the effect of controlling an insect disease and a strawberry fungal disease by *Streptomyces badius* P6C4 strain is confirmed, and the present invention is completed accordingly.

To achieve the aforementioned object, the present invention provides *Streptomyces badius* SP6C4 strain having an antimicrobial activity against an insect pathogen or a strawberry fungal disease pathogen.

The present invention further provides a composition for controlling an insect disease or a strawberry fungal disease containing *Streptomyces badius* SP6C4 strain or a culture thereof as an active ingredient.

The present invention further provides a method for producing a composition for controlling an insect disease or a strawberry fungal disease comprising culturing *Streptomyces badius* SP6C4 strain.

The present invention still further provides a method for controlling an insect disease or a strawberry fungal disease comprising treating an area, a plant, or soil infected with an insect pathogen with an effective amount of *Streptomyces badius* SP6C4 strain or a culture thereof.

According to the present invention, it is confirmed that *Streptomyces badius* SP6C4 strain isolated from strawberry pollen can suppress the growth of an insect pathogen and a pathogen of a strawberry fungal disease. *Streptomyces badius* SP6C4 strain of the present invention can be used as an environmentally friendly biological agrochemical which is free of any environmental contamination yielded as a side effect of an agrochemical or any human toxicity caused by residual agrochemicals. Furthermore, by having an effect of controlling ABF, chalk brood, and strawberry flower mold disease, *Streptomyces badius* SP6C4 strain of the present invention can be very advantageously used in terms of an industrial use.

BRIEF DESCRIPTION OF THE DRAWINGS

FIG. 3 shows a result illustrating the nucleotide sequence of 16S rRNA from *Streptomyces badius* SP6C4 strain which has been isolated from strawberry pollen.

FIGS. 4A and 4B show a result illustrating the antimicrobial activity of *Streptomyces badius* SP6C4 strain isolated from strawberry pollen against an insect pathogen. FIG. 4A indicates the antimicrobial activity against a pathogen causing chalk brood (i.e., Ascosphaera apis), and FIG. 4B indicates the antimicrobial activity against a pathogen causing AFB (i.e., *Paenibacillus larvae*).

DETAILED DESCRIPTION

Figure 1:
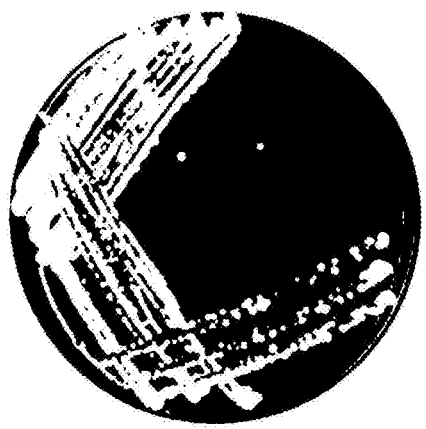
FIG. 1 shows a result illustrating that *Streptomyces badius* SP6C4 strain which has been isolated from strawberry pollen and subcultured in PDA plate medium is a pure-cultured strain.

To achieve the present invention, the present invention provides *Streptomyces badius* SP6C4 strain having an antimicrobial activity against an insect pathogen or a strawberry fungal disease pathogen.

The aforementioned *Streptomyces badius* SP6C4 strain was isolated from strawberry pollen, and it is selected as a strain which has an excellent antimicrobial activity against a pathogen causing chalk brood (i.e., *Ascosphaera apis*), a pathogen causing AFB (i.e., *Paenibacillus larvae*), and also a pathogen causing a strawberry flower mold disease (i.e., *Cladosporium* cladosporioides), which is a strawberry fungal disease pathogen. The aforementioned *Streptomyces badius* SP6C4 strain was duly deposited with Korean Culture Center of Microorganisms (KCCM) (having the address of KCCM, 3F Yurim B/D, 361-221, Hongje-1-dong, Sudaemun-gu, Seoul 120-091, Republic of Korea) under the Access number of KCCM11703P on Jun. 3, 2015. The deposit has been made under the terms of the Budapest Treaty and all restrictions imposed by the depositor on the availability to the public of the biological material will be irrevocably removed upon the granting of a patent.

According to the method of one embodiment of the present invention, the insect pathogen can be a pathogen causing AFB or a pathogen causing chalk brood. It is preferably is *Paenibacilus larvae* or *Ascoshaera apis*, but not limited thereto.

According to the method of one embodiment of the present invention, the strawberry fungal disease pathogen can be a pathogen causing a strawberry flower mold disease. It is preferably *Cladosporium cladosporioides*, but not limited thereto.

The present invention further provides a composition for controlling an insect disease or a strawberry fungal disease containing *Streptomyces badius* SP6C4 strain or a culture thereof as an active ingredient. The composition for controlling an insect disease or a strawberry fungal disease can be used with the meaning of a microbial agrochemical.

The composition for controlling an insect disease or a strawberry fungal disease according to the present invention can be prepared in the form of a solution, powder, a suspension or the like which can be directly sprayed, or a highly concentrated aqueous, oil, or other kind of a suspension, a dispersion, an emulsion, an oil dispersion, a paste, fine powder, a scattering material, or a granular agent, for example, but it is not limited to them.

The composition for controlling an insect disease or a strawberry fungal disease of the present invention can be formulated in various forms. The formulation can be prepared by adding a solvent and/or a carrier, for example. Frequently, an inactive additive and a surface-active material, for example, an emulsifying agent or a dispersing agent, are mixed in a formulation. Examples of a suitable surface-active material include aromatic sulfonic acid (e.g., lagnosulfonic acid, phenol-sulfonic acid, naphthalene- and dibutyl naphthalene sulfonic acid), fatty acid, alkyl- and alkyl aryl sulfonate, alkyl lauryl ether, alkali metal, alkaline earth metal, or ammonium salt of fatty alcohol sulfate, sulfated hexa-, hepta-, and octa decanol, salt of fatty alcohol glycol ether, sulfonate naphthalene and derivatives thereof, condensate of formaldehyde, condensate of naphthalene or naphthalene sulfonic acid, phenol and formaldehyde, polyoxyethylene octylphenol ether, ethoxylated isooctyl-, octyl- or nonyl phenol, alkyl phenyl or tributylphenyl polyglycol ether, alkylaryl polyether alcohol, isotridecyl alcohol, condensate of fatty alcohol/ethylene oxide, ethoxylated castor oil, polyoxyethylene alkyl ether or polyoxypropylene, lauryl alcohol polyglycol ether acetate, sorbitol ester, lignin-sulfite waste, or methyl cellulose, but it is not limited thereto.

A suitable solid carrier material is basically any porous and agriculturally acceptable carrier, and examples thereof include mineral soils (e.g., silica, silica gel, silicate, talc, kaolin, limestone, lime, chalk, boule, yellow soil, clay, dolomite, diatomaceous earth, calcium sulfate, magnesium sulfate, magnesium oxide, and crushed synthetic material), fertilizers (e.g., ammonium sulfate, ammonium phosphate, ammonium nitrate, and urea), plant products (e.g., cereal powder, powder of wood bark, mood meal, and powder of nut shells), and cellulose powder, but it is not limited thereto. Furthermore, the solid carrier can be used either singly or as a mixture of 2 or more types thereof.

The composition for controlling an insect disease or a strawberry fungal disease of the present invention can be used for irrigation with water, spray on leaf surface, sterilization of seeds, or sterilization of farming utensils, or the like, but it is not limited thereto.

The composition for controlling an insect disease or a strawberry fungal disease of the present invention can be used by having, as an active ingredient, *Streptomyces badius* SP6C4 strain only, or by mixing *Streptomyces badius* SP6C4 strain with 2 or more of other antifungal, antimicrobial, or antiviral material.

To enhance the crop absorption and also the effect, the composition for controlling an insect disease or a strawberry fungal disease of the present invention can be also used in combination with other dispersing agent, an infiltrating agent, or a surface active agent.

The present invention further provides a method for controlling an insect disease or a strawberry fungal disease comprising treating an area, a plant, or soil infected with insect pathogen with an effective amount of *Streptomyces badius* SP6C4 strain or a culture thereof.

The method for controlling an insect disease or a strawberry fungal disease can be carried out by scattering the control composition having an effective amount of *Streptomyces badius* SP6C4 strain or a culture thereof to an infected bee house or bee group in an area infected with insect pathogen, by spraying the control composition to a plant or soil, or by dipping a plant in the control composition, but it is not limited thereto.

The "effective amount" described herein indicates an amount that is sufficient for having a beneficial or desired effect. In order to control an insect disease or a strawberry fungal disease, the control composition can be applied, after being homogeneously diluted with water, to a plant or a crop field by using a suitable application device like a motor-driven spreader or the like. When a hydration preparation or a liquid hydration preparation of the present invention is diluted with water, concentration of a hydration preparation or a liquid hydration preparation can be adjusted to $10^5$ to $10^{10}$ cfu/ml, preferably $10^8$ cfu/ml or so, and more preferably $10^6$ cfu/ml so that the active ingredient can be present within a biologically effective range, but it is not limited thereto.

The present invention still further provides a method for producing a composition for controlling an insect disease or a strawberry fungal disease comprising culturing *Streptomyces badius* SP6C4 strain.

As for the method for culturing the strain, any method well known in the pertinent art can be arbitrarily used, and it is not limited to any particular method.

Hereinbelow, the present invention is explained in greater detail in view of the Examples. However, the following Examples are given only for exemplification of the present invention and it would be evident to a skilled person who has common knowledge in the pertinent art that by no means the present invention is limited to the following Examples.

EXAMPLES

Example 1. Isolation of *Streptomyces badius* SP6C4 Strain

To find a strain which has an antimicrobial activity against a pathogen causing chalk brood and a pathogen causing AFB occurring in honey bees in an apiary, strawberry pollen was obtained from the strawberry field in Sugok-myun, Jinjoo-shi, Kyungsangnam-do in South Korea. One gram of the obtained pollen granule was dissolved in 20 ml of PBS buffer. Then, after adding the sample (i.e., 1 g of pollen granule+20 ml of PBS buffer) to an ultrasonic homogenizer, ultrasonication was carried out for 10 minutes. For dilution of the sample, 1 ml of the sample was added to 9 ml of sterilized water followed by repetition of the same operation for 8 times, each with dilution of 1/10 times. Accordingly, the sample was diluted from $10^1$ to $10^9$. Each of the diluted samples (100 μl) was spread on a medium containing ISP2 (4 g of yeast extract, 10 g of malt extract, 4 g of glucose, and 20 g of agar, pH 7.3) and TSA (Tryptic soy agar), and according to a dilution spread method, microbes were isolated (FIG. 1).

Example 2. Analysis of Metagenome from Strawberry Pollen

Figure 2:
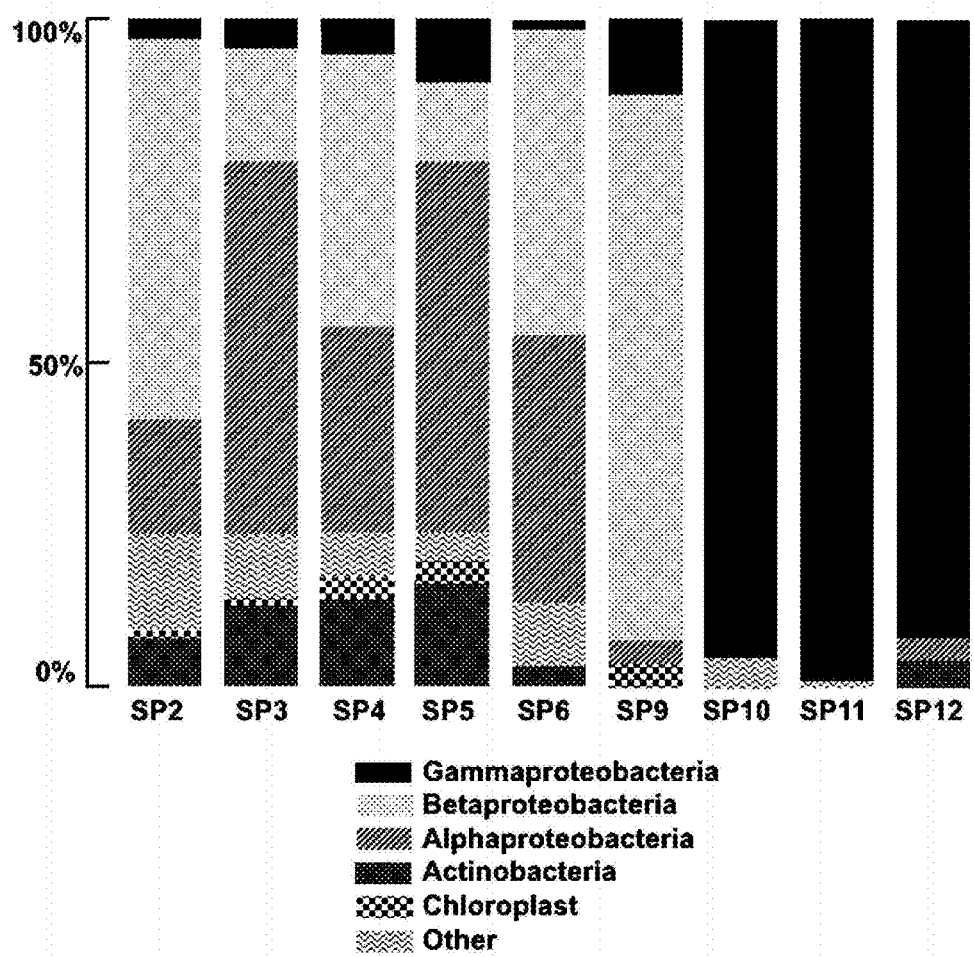
FIG. 2 shows a result of analyzing the metagenome from strawberry pollen.

To analyze the metagenome from strawberry pollen, one gram of the pollen granule was dissolved in 20 ml of PBS buffer. Thereafter, 3 ml of the sample (1 g of pollen granule and 20 ml of PBS buffer) was centrifuged. The obtained pellet was subjected to extraction of genomic DNA by using CTAB (Cetyl trimethyl ammonium bromide) technique. To perform pyrosequencing, the extracted genomic DNA was stored at −20° C. 16S rRNA part of the microbe was amplified, and then subjected to pyrosequencing analysis which is carried out by Macrogen, Inc. (South Korea). All nucleotide sequences were identified by using Silva rRNA database. As a result, as it is shown in FIG. 2, it was confirmed from the metagenome analysis that a microbe of Actinobacteria phylum, in which *Streptomyces* sp. is included, is present in the strawberry pollen.

Example 3. Identification of *Streptomyces badius* SP6C4 Strain

To carry out a molecular biological identification of the isolated microbe, the genomic DNA was isolated and 16S rRNA nucleotide sequence was analyzed (SEQ ID NO: 1). The genomic DNA of *Streptomyces badius* SP6C4 strain was extracted by using CTAB (Cetyl trimethyl ammonium bromide) technique. For the sequencing analysis, primers of the following Table 1, which have V1 to V3 region of 16S rRNA as a target, were used. As a result, as it is shown in FIG. 3, the nucleotide sequence of 16S rRNA was identified as *Streptomyces badius* based on NCBI BLAST search. Furthermore, the strain was named *Streptomyces badius* SP6C4 (Strawberry pollen 6C4) strain.

TABLE 1

| | Primers used in the present invention | | |
|---|---|---|---|
| Primer name | Nucleotide sequence of forward primer (5'-3') | Primer name | Nucleotide sequence of reverse primer (5'-3') |
| 27F | AGAGTTTGATCMTG GCTCAG (SEQ ID NO: 2) | 1492R | GGYTACCTTGTTAC GACTT (SEQ ID NO: 3) |

Example 4. Determination of Antagonistic Activity of *Streptomyces badius* SP6C4 Strain Against Insect Pathogen To determine the antimicrobial activity of *Streptomyces badius* SP6C4 strain, which has been isolated and identified in the above Examples 1 and 3, against an insect pathogen, *Ascosphaera apis* as a pathogen causing chalk brood and *Paenibacillus larvae* as a pathogen causing American foul brood were used. To determine the antimicrobial activity, dual culture of *Streptomyces badius* SP6C4 strain with a pathogen causing chalk brood (*Ascosphaera apis*) or a pathogen causing American foul brood (*Paenibacillus larvae*) was carried out in a PDA plate medium (containing 10 g of potato dextrose, 10 g of peptone, and 20 g of agar). After culturing at 28° C. which is a growth temperature for various pathogens, an observation was made with regard to an inhibition zone. As a result, as it is shown in FIGS. 4A and 4B, it was confirmed that *Streptomyces badius* SP6C4 strain of the present invention exhibits a potent antimicrobial activity against the tested pathogens.

Figure 5:
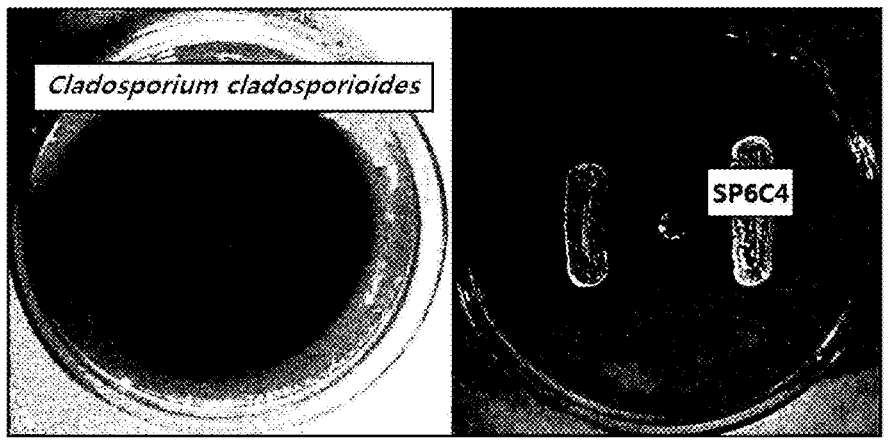
FIG. 5 shows a result illustrating the antimicrobial activity of *Streptomyces badius* SP6C4 strain isolated from strawberry pollen against a pathogen causing a strawberry flower mold disease (i.e., *Cladosporium cladosporioides*).

Example 5. Determination of Antagonistic Activity of *Streptomyces badius* SP6C4 Strain Against Pathogen Causing Strawberry Flower Mold Disease To determine the antimicrobial activity of *Streptomyces badius* SP6C4 strain, which has been isolated and identified in the above Examples 1 and 3, against a pathogen causing a strawberry flower mold disease, dual culture of *Streptomyces badius* SP6C4 strain with a pathogen causing a strawberry flower mold disease (*Cladosporium cladosporioides*) was carried out in a PDA plate medium (containing 10 g of potato dextrose, 10 g of peptone, and 20 g of agar). After culturing at 20° C. according to the characteristic of a low temperature microbe, an observation was made with regard to an inhibition zone. As a result, as it is shown in FIG. 5, it was confirmed that *Streptomyces badius* SP6C4 strain of the present invention exhibits a potent antimicrobial activity against the pathogen causing a strawberry flower mold disease.

Figure 6:
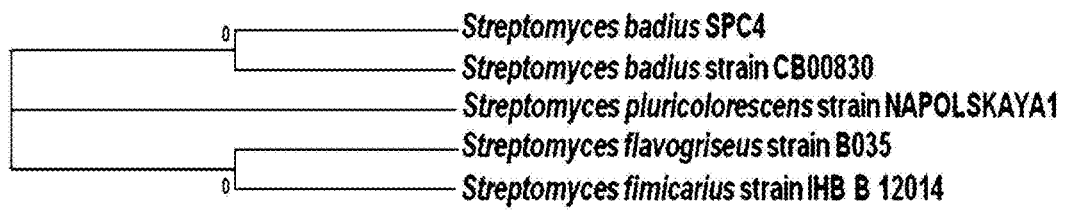
FIG. 6 shows a result of analyzing the phylogenetic relationship of *Streptomyces badius* SP6C4 strain isolated from strawberry pollen, in which the analysis made based on the nucleotide sequence of 16S rRNA.

Example 6. Analysis of Phylogenetic Relationship of *Streptomyces badius* SP6C4 Strain Based on the results of above Example 3, analysis of a phylogenetic relationship was carried out based on the similarity of 16s RNA of the strains belonging to *Streptomyces* sp. that are registered with NCBI. For the analysis of a phylogenetic relationship, Mega 6 program was used. As a result, as it is shown in FIG. 6, it was confirmed that *Streptomyces badius* SP6C4 strain has phylogenetic relationship of 99% with *Streptomyces badius* strain CB00830.

Example 7. Determination of Surviving Ability of *Streptomyces badius* SP6C4 Strain in Strawberry Flower To determine the surviving ability of *Streptomyces badius* SP6C4 strain in strawberry flower, a lab test was carried out. The flower was collected from a strawberry field, and after fixing the stem part in an oasis, the mixture solution (containing 0.1% methyl cellulose, $10^8$ cfu/ml of strain culture, and 10 ml of sterilized water) was first adjusted to an inoculation concentration of $10^6$ cfu/ml and then inoculated by a spray method or a dipping method to the strawberry flower. Next, on Day 5 after the inoculation, the flower was added to 1× buffer, and subjected to an ultrasonication treatment for 5 minutes. After serial dilution of from $10^1$ to $10^9$ (cfu/ml) with sterile water, CFU was measured from $10^4$ to $10^6$ (cfu/ml) each based on dilution spread method.

Figure 7:
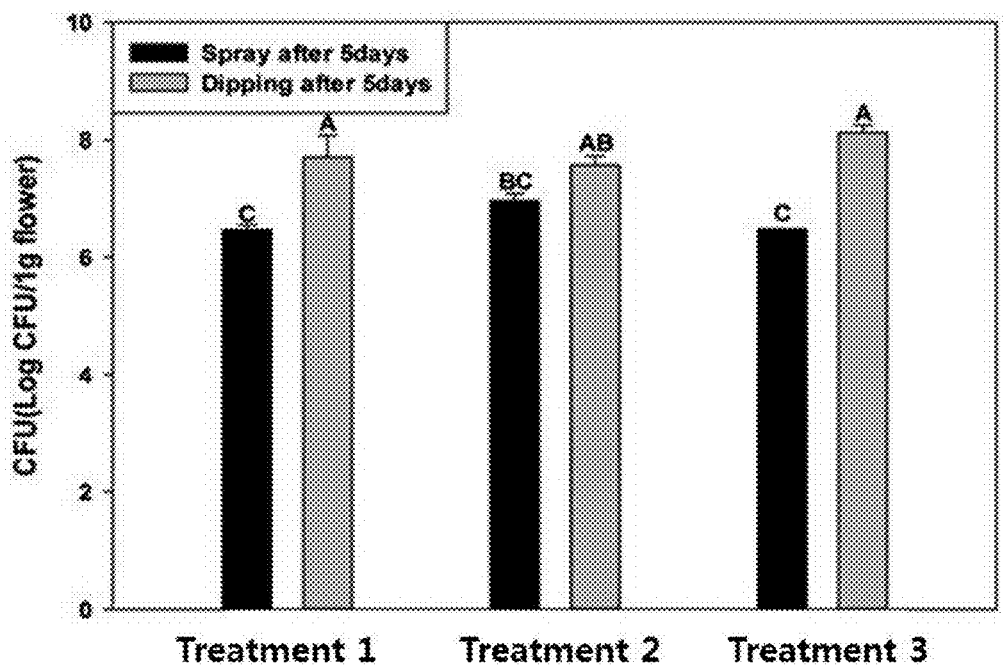
FIG. 7 shows a result of analyzing the surviving ability of *Streptomyces badius* SP6C4 strain in strawberry flower. The treatment 1 corresponds to a test group treated with *Streptomyces badius* SP6B4 strain, the treatment 2 corresponds to a test group treated with *Streptomyces badius* SP6C4 strain, and the treatment 3 corresponds to a test group treated with *Streptomyces badius* SP12C7 strain.

As a result, it was found as it is shown in FIG. 7 that, according to the spray method, the highest survival rate in strawberry flower was obtained from a treatment with *Streptomyces badius* SP6C4 strain (i.e., treatment 2), while according to the dipping method, the highest survival rate in strawberry flower was obtained from a treatment with *Streptomyces* sp. SP12C7 strain (i.e., treatment 3).

Thus, as the density of $10^5$ (cfu/ml) exhibiting an antimicrobial activity of a microbe used for control of an insect disease and a plant disease is maintained in the present invention, a possibility of developing the strain as a microbial preparation is confirmed. In addition, as the high survival rate is shown with a spray method that is similar to a method for applying agrochemicals, it is believed that *Streptomyces badius* SP6C4 strain has a high potential of development into a commercial product.

The invention claimed is:

1. A method for controlling an insect disease or a strawberry fungal disease comprising treating an area, a plant, or soil infected with insect pathogen or a strawberry fungal disease pathogen with an effective amount of *Streptomyces badius* SP6C4 strain deposited with Korean Culture Center of Microorganisms (KCCM) under the accession number of KCCM11703P, wherein when the method is for controlling the insect disease, the insect pathogen is a pathogen causing American foul brood or a pathogen causing chalk brood; and when the method is for controlling the strawberry fungal disease, the strawberry fungal disease pathogen is a pathogen causing a strawberry flower mold disease.

2. The method of claim 1, wherein the method is for controlling the insect disease, and the insect pathogen is the pathogen causing American foul brood or the pathogen causing chalk brood.

3. The method of claim 2, wherein the pathogen causing American foul brood is *Paenibacillus larvae*, and the pathogen causing chalk brood is *Ascosphaera apis*.

4. The method of claim 1, wherein the method is for controlling the strawberry fungal disease, and the strawberry fungal disease pathogen is the pathogen causing the strawberry flower mold disease.

5. The method of claim 4, wherein the pathogen causing a strawberry flower mold disease is *Cladosporium* cladosporioides.

* * * * *

SEQUENCE LISTING

<160> NUMBER OF SEQ ID NOS: 3

<210> SEQ ID NO 1
<211> LENGTH: 1208
<212> TYPE: DNA
<213> ORGANISM: Streptomyces badius

<400> SEQUENCE: 1

| | | | | | |
|---|---|---|---|---|---|
| gctcaggacg | aacgctggcg | gcgtgcttaa | cacatgcaag | tcgaacgatg | aagcccttcg | 60 |
| gggtggatta | gtggcgaacg | ggtgagtaac | acgtgggcaa | tctgcccttc | actctgggac | 120 |
| aagccctgga | aacgggtct | aataccggat | aacactctgt | cccgcatggg | acggggttga | 180 |
| aagctccggc | ggtgaaggat | gagcccgcgg | cctatcagct | tgttggtggg | gtaatggcct | 240 |
| accaaggcga | cgacgggtag | ccggcctgag | agggcgaccg | gccacactgg | gactgagaca | 300 |
| cggcccagac | tcctacggga | ggcagcagtg | gggaatattg | cacaatgggc | gaaagcctga | 360 |
| tgcagcgacg | ccgcgtgagg | gatgacggcc | ttcgggttgt | aaacctcttt | cagcagggaa | 420 |
| gaagcgaaag | tgacggtacc | tgcagaagaa | gcgccggcta | actacgtgcc | agcagccgcg | 480 |
| gtaatacgta | gggcgcaagc | gttgtccgga | attattgggc | gtaaagagct | cgtaggcggc | 540 |
| ttgtcacgtc | ggatgtgaaa | gcccggggct | taaccccggg | tctgcattcg | atacgggcta | 600 |
| gctagagtgt | ggtaggggag | atcggaattc | ctggtgtagc | ggtgaaatgc | gcagatatca | 660 |
| ggaggaacac | cggtggcgaa | ggcggatctc | tgggccatta | ctgacgctga | ggagcgaaag | 720 |
| cgtggggagc | gaacaggatt | agataccctg | gtagtccacg | ccgtaaacgt | tgggaactag | 780 |
| gtgttggcga | cattccacgt | cgtcggtgcc | gcagctaacg | cattaagttc | cccgcctggg | 840 |
| gagtacggcc | gcaaggctaa | aactcaaagg | aattgacggg | ggcccgcaca | agcagcggag | 900 |
| catgtggctt | aattcgacgc | aacgcgaaga | accttaccaa | ggcttgacat | ataccggaaa | 960 |
| gcatcagaga | tggtgccccc | cttgtggtcg | gtatacaggt | ggtgcatggc | tgtcgtcagc | 1020 |
| tcgtgtcgtg | agatgttggg | ttaagtcccg | caacgagcgc | aacccttgtt | ctgtgttgcc | 1080 |
| agcatgccct | tcggggtgat | ggggactcac | aggagactgc | cggggtcaac | tcggaggaag | 1140 |
| gtggggacga | cgtcagtcat | catgccccctt | atgtcttggg | ctgcacacgt | gctacaatgg | 1200 |
| ccggtaca | | | | | | 1208 |

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
agagtttgat cmtggctcag      20

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
ggytaccttg ttacgactt      19